United States Patent
Zhu

(10) Patent No.: US 11,234,633 B2
(45) Date of Patent: Feb. 1, 2022

(54) GROUP APPLICATION ORIENTED TRANSCRANIAL BRAIN ATLAS GENERATION METHOD, PREDICTION METHOD AND PREDICTION APPARATUS

(71) Applicant: BEIJING NORMAL UNIVERSITY, Beijing (CN)

(72) Inventor: Chaozhe Zhu, Beijing (CN)

(73) Assignee: BEIJING NORMAL UNIVERSITY, Beijing (CN)

( * ) Notice: Subject to any disclaimer, the term of this patent is extended or adjusted under 35 U.S.C. 154(b) by 484 days.

(21) Appl. No.: 16/314,650

(22) PCT Filed: Apr. 22, 2018

(86) PCT No.: PCT/CN2018/083999
§ 371 (c)(1),
(2) Date: Dec. 31, 2018

(87) PCT Pub. No.: WO2019/109574
PCT Pub. Date: Jun. 13, 2019

(65) Prior Publication Data
US 2021/0225004 A1  Jul. 22, 2021

(30) Foreign Application Priority Data

Dec. 5, 2017 (CN) .......................... 201711268640.0
Dec. 12, 2017 (CN) .......................... 201711322471.4

(51) Int. Cl.
| | |
|---|---|
| *A61B 5/00* | (2006.01) |
| *A61B 5/05* | (2021.01) |
| *G06F 3/0354* | (2013.01) |
| *G06T 17/20* | (2006.01) |

(Continued)

(52) U.S. Cl.
CPC .............. *A61B 5/4064* (2013.01); *A61B 5/05* (2013.01); *A61B 8/08* (2013.01); *G06F 3/03545* (2013.01);

(Continued)

(58) Field of Classification Search
CPC ..................... G06T 7/143; G06T 19/20; G06T 2207/30016; G06T 2207/10088; G06T 2210/56; G06T 2210/41
See application file for complete search history.

(56) References Cited

U.S. PATENT DOCUMENTS

2005/0171558 A1    8/2005  Abovitz et al.
2018/0310854 A1 *  11/2018  Geva ................... A61B 5/7242

FOREIGN PATENT DOCUMENTS

CN    101515367 A      8/2009
CN    105854193 A  *   8/2016  ............... A61N 7/00
(Continued)

OTHER PUBLICATIONS

Okamoto, M. and Dan, I., 2005. Automated cortical projection of head-surface locations for transcranial functional brain mapping. Neuroimage, 26(1), pp. 18-28.*

(Continued)

*Primary Examiner* — Zhitong Chen
(74) *Attorney, Agent, or Firm* — Ladas & Parry, LLP

(57) ABSTRACT

The present invention discloses a transcranial brain atlas generation method, and discloses a group application oriented transcranial brain atlas prediction method and a corresponding transcranial brain atlas prediction apparatus. The transcranial brain atlas generation method includes the following steps: creating a cranial surface coordinate system at an individual level; establishing a transcranial mapping system used to connect a cranial location and a brain location; and constructing a transcranial brain atlas by using a two-step stochastic process in a Markov chain. According to the transcranial brain atlas provided in the present invention, invisible intracerebral atlas label information is projected onto a visible scalp, so that a researcher or a doctor may "directly" use these pieces of brain structure informa- (Continued)

tion and function atlas information, thereby greatly improving the function of the brain atlas during use of a transcranial brain mapping technology.

14 Claims, 5 Drawing Sheets

(51) Int. Cl.
*G06T 7/143* (2017.01)
*G06T 19/20* (2011.01)
*A61B 8/08* (2006.01)
*G06T 19/00* (2011.01)

(52) U.S. Cl.
CPC .............. *G06T 7/143* (2017.01); *G06T 17/20* (2013.01); *G06T 19/00* (2013.01); *G06T 19/20* (2013.01); *A61B 2560/0223* (2013.01); *G06T 2207/10088* (2013.01); *G06T 2207/30016* (2013.01); *G06T 2210/41* (2013.01); *G06T 2210/56* (2013.01)

(56) References Cited

FOREIGN PATENT DOCUMENTS

| CN | 106920228 A | 7/2017 |
|----|-------------|--------|
| TW | 499308 B    | 8/2002 |

OTHER PUBLICATIONS

Fischl, B., Van Der Kouwe, A., Destrieux, C., Halgren, E., Ségonne, F., Salat, D.H., Busa, E., Seidman, L.J., Goldstein, J., Kennedy, D. and Caviness, V., 2004. Automatically parcellating the human cerebral cortex. Cerebral cortex, 14(1), pp. 1 1-22.*

International Search Report from PCT/CN2018/083999, dated Apr. 10, 2019, with English translation provided by WIPO.

Written Opinion of the International Searching Authority from PCT/CN2018/083999, dated Apr. 10, 2019, with English translation provided by Google translate.

* cited by examiner

GROUP APPLICATION ORIENTED TRANSCRANIAL BRAIN ATLAS GENERATION METHOD, PREDICTION METHOD AND PREDICTION APPARATUS

CROSS-REFERENCE TO RELATED APPLICATIONS

The present application is the U.S. national phase of PCT Application PCT/CN2018/083999 filed on Apr. 22, 2018, which claims priority to the Chinese patent application No. 201711268640.0 filed on Dec. 5, 2017, and Chinese patent application No. 201711322471.4 filed on Dec. 12, 2017, the entire disclosures of which are hereby incorporated by reference in their entireties.

BACKGROUND

Technical Field

The present invention relates to a transcranial brain atlas generation method, also relates to a group application oriented transcranial brain atlas prediction method, and further relates to a corresponding transcranial brain atlas prediction apparatus.

Related Art

Currently, an important task with which the cognitive neuroscience is confronted is to establish a correspondence between a brain function and a brain structure. Functional brain imaging technologies represented by the functional magnetic resonance imaging (fMRI) and the functional near-infrared spectroscopy (fNIRS) enable researchers of the neuroscience to observe a function of a living human brain in a non-invasive manner.

In an existing functional brain imaging technology, a transcranial imaging apparatus placed on a cranial surface is usually used to observe and intervene in an intracranial cerebral activity, and therefore the functional brain imaging technology is also referred to as a transcranial brain imaging technology. A concept of two spaces exists in the transcranial brain imaging technology, where one space is a cranial surface space visible to the transcranial imaging apparatus, and the other space is an intracranial brain space invisible to the transcranial imaging apparatus. Separation between the two spaces causes problems in two aspects of positioning function data and correctly placing the transcranial imaging apparatus in the transcranial imaging technology. A key to resolving these problems is to establish a correspondence between the two spaces.

The transcranial brain imaging technology itself can provide only brain function information, but cannot provide brain structure information, and can only position the obtained brain function information to the cranial surface space in which the transcranial imaging apparatus is located, but not the intracranial brain space in which the human brain is located. This disables the transcranial brain imaging technology from positioning transcranial brain imaging data to a standard brain space (that is, MNI space) under a conventional brain imaging positioning framework. This also means that a reference system in conventional brain imaging research established based on the standard brain space and a brain atlas cannot be directly applied to the transcranial brain imaging technology.

The brain atlas (BA for short) is an important standard reference system in brain imaging research. First, the brain atlas provides a standard platform for brain imaging research, so that results of different researches carried out based on different subject brains can be compared and verified with each other, thereby comprehensively understanding the brain function architecture. Second, priori knowledge about the human brain provided in the brain atlas is the basis of designating a region of interest and a brain network node in the brain imaging research, and is also the basis of explaining and reporting a brain imaging result. Therefore, a step of positioning the brain function data to the standard brain space in which the brain atlas is located is necessary for the brain imaging research and analysis. However, in the existing transcranial brain imaging technology, a general brain atlas model having a scientific basis and having predictability for different populations is not provided. In practice, separation between a visible operational space (that is, scalp surface, and in particular, upper scalp surface) and an invisible effective space (that is, intracranial brain space) is still one of biggest challenges in effectively applying a transcranial brain mapping technology.

SUMMARY

A primary technical problem to be resolved by the present invention is to provide a transcranial brain atlas generation method. By using a transcranial brain atlas, invisible intracerebral atlas information may be projected onto a visible scalp surface, so that an operational space and an effective space that are originally separated are fused together.

Another technical problem to be resolved by the present invention is to provide a group application oriented transcranial brain atlas prediction method.

Still another technical problem to be resolved by the present invention is to provide a group application oriented transcranial brain atlas prediction apparatus.

To achieve the foregoing objective, the present invention uses the following technical solutions:

According to a first aspect of embodiments of the present invention, a transcranial brain atlas generation method is provided, including the following steps:

(1) creating a cranial surface coordinate system at an individual level;

(2) establishing a transcranial mapping system used to connect a cranial location and a brain location; and (3) constructing a transcranial brain atlas by using a two-step stochastic process in a Markov chain.

Preferably, the step (1) includes the following substeps:

(11) identifying five cranial landmarks Nz, Iz, AL, AR, and Cz on a scalp surface;

(12) defining an intersection curve between the scalp surface and a plane passing through Nz, Cz, and Iz as a cranial equator;

(13) giving a point p on the scalp surface, where a longitude curve can be uniquely determined as an intersection curve between the scalp surface and a plane passing through AL, AR, and p, and p' is an intersection point between the cranial equator and the longitude curve; and

(14) uniquely determining any point p on an upper scalp by using a pair of non-negative real numbers $(p_e, p_l)$:

$$p_e = L_{Nz\text{-}p'}/L_e, p_e \in [01]$$

$$p_l = L_{AL\text{-}p}/L_{AL\text{-}p\text{-}AR}, p_l \in [01]$$

where $L_{Nz\text{-}p'}$ is a curve length from Nz to p' along the cranial equator, and $L_e$ is a full length of the cranial equator; and $L_{AL\text{-}p}$ is a curve length from AL to p along the longitude curve whose full length is $L_{AL\text{-}p\text{-}AR}$.

Preferably, the step (1) further includes step (15): establishing a CPC space on a standard hemisphere; and planarizing a hemisphere having CPC coordinates by using a Hammer-Aitoff projection, to generate a map having a CPC coordinate system presented on a flat ellipse.

Preferably, the step (2) includes the following substeps: determining an underlying cortical location c corresponding to the given any point p on the scalp surface in an individual space by using a balloon inflation model; and after all cortical locations are spatially normalized into an MNI space, aggregating all (p, c) pairs, to generate a deterministic individual transcranial brain mapping model.

Preferably, the step (2) further includes the following step:

integrating all individual models to generate a group-level probabilistic transcranial brain mapping model: P(c|p), where $p(p_e, p_l) \in CPC$, $c(x, y, z) \in C$, and C is a subset of the MNI space.

Preferably, in the step (2), the probabilistic transcranial brain mapping model is generated according to the following formula:

$$P(c_j|p_i) = \frac{\text{total number of individuals whose } CPC \text{ point } p_i \text{ is mapped to an } MNI \text{ location } c_j}{\#}$$

where $p_i$ is a $CPC_{100}$ grid location, where $i=1, 2, \ldots, N_p$; $c_j$ is a cortical voxel in the MNI space obtained by using a transcranial brain mapping technology, where $j=1, 2, \ldots, N_c$; and # is a total number of individuals.

Preferably, the step (3) further includes the following steps:

(31) mapping a given point p ($p_e$, $p_l$) to a cortical location c (x, y, z) in the MNI space through probabilistic transcranial mapping P(c|p); and

(32) mapping the cortical location c (x, y, z) to a label l in a label space L.

Preferably, in the step (3), assuming that points on a cortical domain c are a subset of points on a cerebral domain b, if p and c are discretized, P(l|p) is indicated by using a Chapman-Kolmogorov equation:

$$P(l_k|p_i) = \sum_{j=1}^{N_C} P(l_k|c_j) \times P(c_j|p_i)$$

where $p_i$ is a discretized location in a CPC space, where $i=1, 2, \ldots, N_p$; $c_j$ is a discretized location of C in the MNI space, where $j=1, 2, \ldots, Nc$; and $l_k$ is a label of a particular brain atlas, where $k=1, 2, \ldots, N_l$.

Preferably, in the step (32), any one of an LPBA40 brain atlas, an AAL labeling atlas or a Talairach atlas is used.

Preferably, the transcranial brain atlas generation method further includes step (4): generating a maximum likelihood labeling map and/or a maximum probability map.

According to a second aspect of the embodiments of the present invention, a group application oriented transcranial brain atlas prediction method is provided, including the following step:

for an independent individual in a group, when a probe of a transcranial device performs stimulation or recording at any location on a scalp surface having given coordinates, giving, by using the foregoing transcranial brain atlas, a probability that each targeted brain region is probed.

Preferably, the transcranial device is any one of a transcranial brain imaging apparatus or a transcranial brain treatment apparatus.

According to a third aspect of the embodiments of the present invention, a group application oriented transcranial brain atlas prediction apparatus is provided, for implementing the foregoing transcranial brain atlas prediction method, where the transcranial brain atlas prediction apparatus is in a shape of a helmet or a head cap, and has an upper surface covered with the foregoing transcranial brain atlas and a lower surface tightly attached to a scalp surface of a user during use.

Preferably, a plurality of small holes is distributed on a surface of the transcranial brain atlas prediction apparatus, so as to enable a probe of a transcranial device to be in contact with the scalp surface of the user through the small holes.

Preferably, the small holes are arranged into a dot matrix shape according to different sub-regions in a transcranial brain atlas image, and have an arrangement density reversely changed according to the area of the sub-regions.

According to the transcranial brain atlas provided in the present invention, invisible intracerebral atlas label information is projected onto a visible scalp, so that a researcher or a doctor may "directly" use these pieces of brain structure information and function atlas information, thereby greatly improving the function of the brain atlas during use of the transcranial brain mapping technology. Moreover, according to the transcranial brain atlas, an operational space and an effective space that are originally separated are fused together, so that an operator operates like operating on a brain space. This enables inherent issues such as positioning in the transcranial brain mapping technology to be resolved more thoroughly.

DETAILED DESCRIPTION

Figure 1:
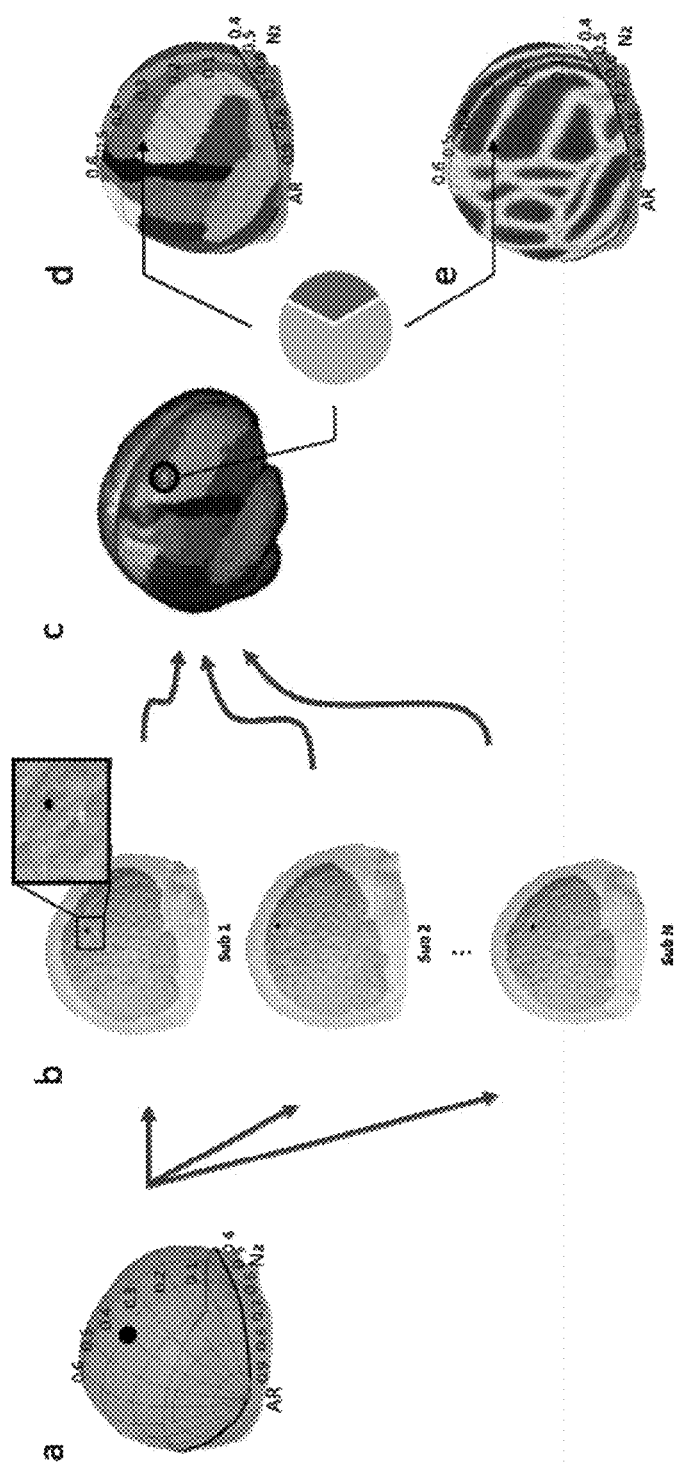
FIG. 1(a) to FIG. 1(e) are schematic diagrams of a series of embodiments of a transcranial brain atlas.

Technical content of the present invention is further described in detail below with reference to the accompanying drawings and specific embodiments.

As described above, separation between a cranial surface space visible to a transcranial imaging apparatus and an intracranial brain space invisible to the transcranial imaging apparatus is one of biggest challenges in effectively applying a transcranial brain mapping technology. To resolve a corresponding problem of the two spaces, the present invention first proposes a concept of a transcranial brain atlas (TBA for short). The transcranial brain atlas is a brain atlas established on a scalp surface. According to the transcranial brain atlas, invisible intracerebral atlas information is projected onto a visible scalp surface (particularly, upper scalp surface), so that a researcher or a doctor may directly use these pieces of atlas information related to the brain structure and the brain function.

Specifically, in the present invention, a standard cranial coordinate system is explicitly constructed first, and used to quantitatively describe cranial surface spaces for different individuals. Then, according to an assumption of consistency of a cranio-cerebral correspondence at a population level, a correspondence between a standard cranial surface space and a standard brain space in which a brain atlas is located is established. Finally, according to the present invention, from two correspondences between the cranial surface space and the standard brain space, and between the standard brain space provided in the brain atlas and a brain region label space, a correspondence between the cranial surface space and the brain region label space is solved. As a result, in the present invention, information in the standard brain space and the brain atlas that are corresponding to each other is reversely presented to the cranial coordinate system, thereby forming a novel "transcranial brain atlas". The transcranial brain atlas has an important property of being capable of directly deducing information about a corresponding brain region label by using only information about a cranial location, and therefore may be roughly understood as a brain atlas established on a scalp surface. The transcranial brain atlas is substantially a brain function map established on a coordinate-based scalp surface. That is, in a coordinate-based brain space, a conventional brain atlas corresponds to each cerebral location and a functional or anatomical label thereof, thereby drawing cortical locations accessible to a transcranial brain mapping technology and atlas labels corresponding to the cortical locations, and clearly and definitely presenting them on the scalp surface as a visible operational space. In the transcranial brain atlas, priori brain region information in the conventional brain atlas may be mapped to a cranial space used to place a transcranial brain imaging apparatus in the sense of a population-level cranio-cerebral correspondence. Therefore, the transcranial brain atlas may be considered as an extension of the conventional brain atlas in the field of transcranial imaging technologies. Under the framework of the transcranial brain atlas, positioning for transcranial data in the brain space may be converted into positioning for the transcranial imaging apparatus in the cranial space, so that real-time positioning of the transcranial brain mapping technology becomes possible. Moreover, label information of the transcranial brain atlas is displayed in the cranial space, and this characteristic greatly helps the transcranial brain atlas be superposed onto a scalp surface of an individual to perform display, thereby guiding placement of the transcranial imaging apparatus on a cranial surface of a subject in a visual manner. Therefore, establishment of the transcranial brain atlas resolves a contradiction of separation between the operational space and the effective space in the transcranial brain mapping technology.

FIG. 1(a) to FIG. 1(e) are schematic diagrams of a series of embodiments of a transcranial brain atlas. As shown in FIG. 1(a), it is assumed that a unified cranial surface coordinate system is defined on a scalp surface. The cranial surface coordinate system describes all possible locations at which a probe for a transcranial brain mapping technology may be disposed, and the probe is disposed at a given cranial location (a location of a black point in the figure). For a particular individual (for example, a subject sub 1 in FIG. 1(b)), a probe disposed on a scalp surface of the subject can probe a particular cortical location/brain region (a location of a yellow point in the figure). However, at a group level, in consideration of a difference between anatomical structures across individuals, such a cranio-cerebral correspondence may not be deterministic. As shown in FIG. 1(c), after normalized into the standard brain space, the space distribution (that is, colored region within a black circle) of such a probabilistic correspondence is captured. By giving anatomical information obtained from the brain atlas, such a probabilistic correspondence can provide a group-level probability of how to access each brain region from a cranial location, and the group-level probability is used as priori knowledge. The transcranial brain atlas is substantially used for mapping the priori knowledge to the entire brain space defined by the cranial surface coordinate system. Specifically, in the series of embodiments shown in FIG. 1, if only a most possibly probed brain region label and a probability associated with the brain region label are considered for each cranial location, the maximum likelihood labeling map (MLM) shown in FIG. 1(d) and the maximum probability map (MPM) shown in FIG. 1(e) may be used as useful guidance for probe arrangement in the transcranial brain mapping technology.

In the embodiments of the present invention, a process of generating a transcranial brain atlas mainly includes three steps: (1) creating a cranial surface coordinate system at an individual level; (2) establishing a transcranial mapping system used to connect a cranial location and a brain location; and (3) constructing a transcranial brain atlas by using a two-step stochastic process in a Markov chain.

A detailed process for generating the transcranial brain atlas is described below.

(1) Create a Cranial Surface Coordinate System at an Individual Level

The cranial surface coordinate system needs to satisfy two basic requirements: first, it should provide a one-to-one mapping for the individual scalp surface; and second, for the convenience of group-level studies, it should make, for each location in the cranial surface coordinate system, the underlying cortical locations from different individuals basically consistent with each other neural-anatomically.

Figure 2:
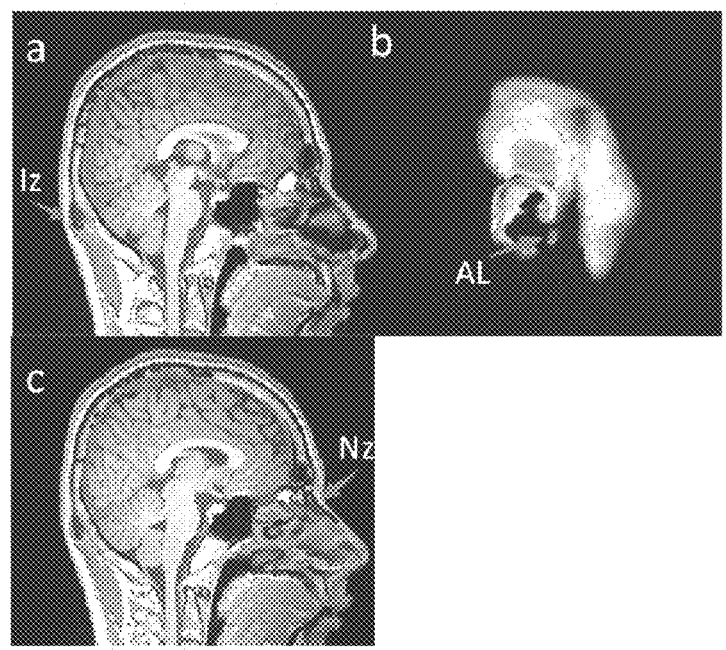
FIG. 2 is a schematic diagram of identifying a cranial landmark from a magnetic resonance image.
Figure 3:
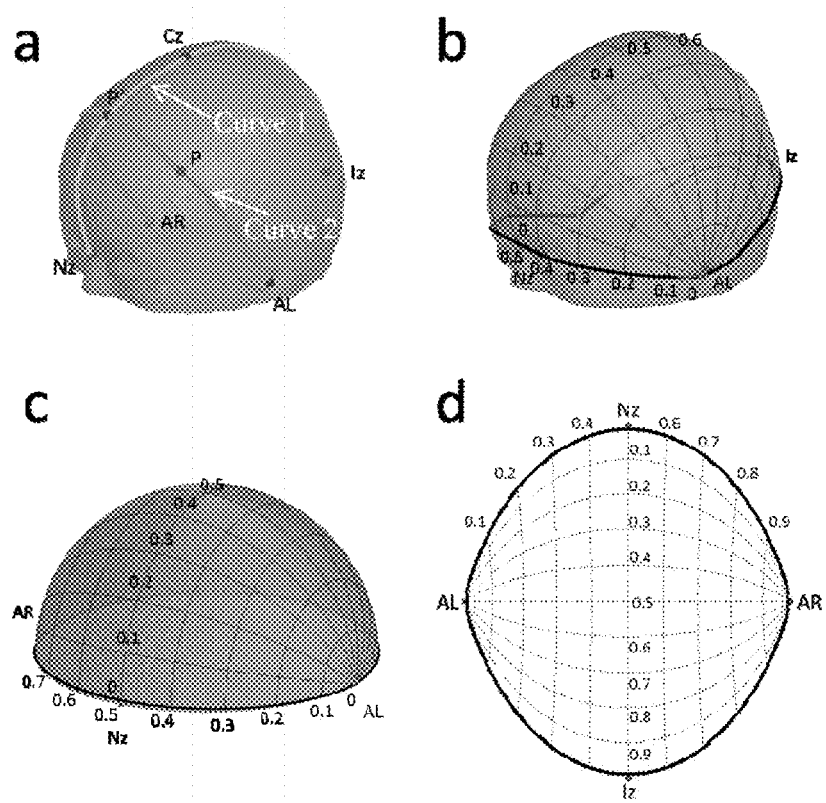
FIG. 3 is a schematic diagram of a CPC coordinate system.

The basic idea of the CPC coordinate system is to construct a coordinate system similar to longitude and latitude lines on a head surface. Different from a geographic longitude and latitude line system, the CPC coordinate system determines "longitude and latitude" in a manner of performing surface proportion measurement twice. In the embodiments of the present invention, by using the following three steps, a two-dimensional proportional coordinate system referred to as a continuous proportional coordinate space (CPC space for short) is established on a scalp surface of an individual:

(11) At least five cranial landmarks Nz, Iz, AL, AR, and Cz derived from a 10-20 system are identified on a scalp surface of an individual space (referring to FIG. 3(a)). For an example of identifying a cranial landmark in a magnetic resonance image, refer to FIG. 2, where Iz is an external occipital protuberance of a human cranial bone onto which a trapezius is attached; AL and AR are left and right preauricular points that are identified as peak regions of tragi; Nz is identified as a dent location on a superior root of a nose bridge; and Cz is determined as an intersection point of cranial surface geodesics AL-Cz-AR and Nz-Cz-Iz, and equally divides the two cranial surface geodesics.

(12) A cranial equator is defined as an intersection curve (that is, a curve 1 in FIG. 3(a)) between the scalp surface and a plane passing through Nz, Cz, and Iz.

(13) A point p is given on the scalp surface, where a longitude curve (that is, a curve 2 in FIG. 3(a)) can be uniquely determined as an intersection curve between the scalp surface and a plane passing through AL, AR, and p, and p' is an intersection point between the cranial equator and the longitude curve.

On the basis of the three-step definition, any point p on an upper scalp (above the curve specified by the Nz, Iz, AL, and AR points) can be uniquely determined by using a pair of non-negative real numbers $(p_e, p_l)$:

$$p_e = L_{Nz-p'}/L_e, p_e \in [01] \quad (1)$$

$$p_l = L_{AL-p}/L_{AL-p-AR}, p_l \in [01] \quad (2)$$

where $L_{Nz-p'}$ is a curve length from Nz to p' along the cranial equator, and $L_e$ is a full length (from Nz to Iz) of the cranial equator; and $L_{AL-p}$ is a curve length from AL top along the longitude curve whose full length is $L_{AL-p-AR}$. As shown in FIG. 3(b), a surface location of the p point as any point is uniquely indicated by proportions of p' and p respectively relative to the two curves. For calculation formulas, refer to the formula (1) and the formula (2).

FIG. 3(b) is a schematic diagram of a two-dimensional proportional coordinate system (CPC coordinate system for short) established on a scalp surface. The two-dimensional proportional coordinate system provides one-to-one mapping for any point p on the scalp surface to the CPC space. Based on an inter-subject correspondence established according to a proportional relationship defined between the cranial landmarks (Nz, Iz, AL, AR, and Cz) and the CPC coordinate system (proportional to the scale and the shape), a proper anatomical correspondence may be established on an individual-level scalp surface. To visualize the entire scalp surface from a single viewing angle, as shown in FIG. 3(c), a special CPC space is established on a standard hemisphere. Then, a hemisphere having a CPC coordinate system is planarized by using an existing Hammer-Aitoff projection, to generate a map having the CPC coordinate system presented on a flat ellipse. The applicant names the map a BNU map (Beijing Normal University Map) (referring to FIG. 3(d)), which is actually a two-dimensional projection image of a standard CPC coordinate system. On the basis of the BNU map, any brain function data related to the scalp surface can be presented in the map, thereby implementing an efficient comparison between different projects, populations, laboratories and even different imaging modalities.

(2) A transcranial brain mapping (TBM for short) model used to connect a cranial location and a brain location is established.

Once the CPC space is established on the individual-level scalp surface, by using a mature balloon inflation model (Okamoto & Dan, 2005), an underlying cortical location c corresponding to the given any point p on the scalp surface may be determined in an individual space (for example, individual 3D MRI image). After all cortical locations are spatially normalized into a standard brain space (that is, MNI space), all (p, c) pairs are aggregated, and a deterministic individual transcranial brain mapping model may be generated. Then, a group-level probabilistic transcranial brain mapping model is generated by integrating all individual transcranial brain mapping models:

$$P(c|p) \quad (3)$$

$p(p_e, p_l) \in CPC$, $c(x, y, z) \in C$, and C is a subset of the standard brain space and contains all cortical locations related to the transcranial brain mapping technology. The probabilistic transcranial brain mapping model gives the probability of each targeted cortical location c(x, y, z) when stimulation or recording starts from any point $p(p_e, p_l)$ having given coordinates on the scalp surface.

Figure 4:
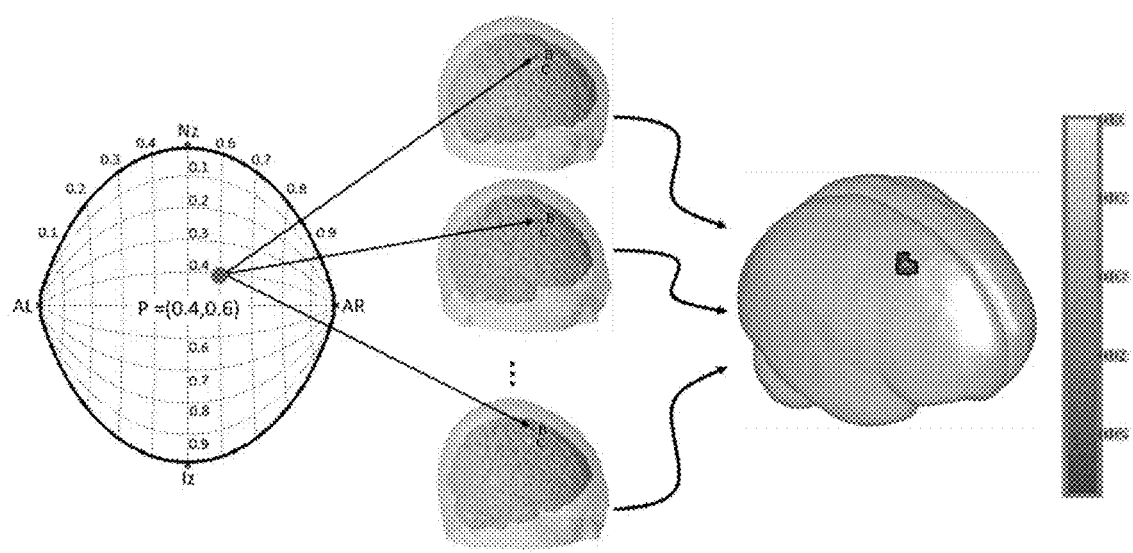
FIG. 4 is a schematic diagram of probabilistic transcranial brain mapping of a single CPC coordinate point.

FIG. 4 shows a probabilistic transcranial brain mapping model corresponding to a single CPC coordinate. When a pair of CPC coordinates is given, for example, P=(0.4, 0.6), a corresponding point B may be determined on each individual-level scalp surface, and a location of a cortical projection point C corresponding to the point B is identified in an individual-level magnetic resonance image space by using the mature balloon inflation model. In FIG. 4, a table on the lower half shows corresponding probabilities that any point P=(0.4, 0.6) corresponds to different locations in a probabilistic transcranial mapping model.

Mapping from a point in a cranial space to a label in a label space may be considered as two-step mapping. First, mapping is made from the cranial space S to a brain space B, and then mapping is made from the brain space B to the label space L. Because both steps of the mapping are probability mapping, this process may also be considered as a two-step stochastic process. A correspondence between the brain space and a brain region label depends on the structural law of a human brain, and it is assumed that a probability that any point in the brain coordinate space corresponds to each brain region label is deterministic and is unrelated to a corresponding path from the cranial coordinate space to the brain coordinate space. Therefore, this two-step stochastic process has a Markov property.

(3) A transcranial brain atlas is constructed by using a two-step stochastic process in a Markov chain.

A person skilled in the art knows that, the brain atlas is constructed in a probability framework. For example, a fundamental relationship described by a conventional brain atlas (for example, MNI atlas) is a conditional probability:

$$P(l|b) \quad (4)$$

where $b(x, y, z) \in B$, and B is the subset of the standard brain space and contains all possible brain tissue points in a brain template of the atlas; and $l \in L$, L contains all possible atlas labels, and each atlas label indicates a particular brain region in the brain atlas. For a given pair of l and b, P(l|b) indicates a possibility that an atlas label l occurs at a location b in the human brain.

Correspondingly, a fundamental relationship describe by a transcranial brain atlas is also a conditional probability:

$$P(l|p) \quad (5)$$

where $p(p_e, p_l) \in CPC$, and $l \in L$.

In an embodiment of the present invention, a transcranial brain atlas may be constructed by using a two-step stochastic process in a Markov chain. Specifically, first step: a given point $p(p_e, p_l)$ as input is mapped to a cortical location c(x, y, z) in the standard brain space through probabilistic transcranial mapping P(c|p). Second step: the particular c(x, y, z) is mapped to a label l in a label space L. A researcher or a doctor may independently predict the atlas label l by using the cortical location c(x, y, z) without considering the location $p(p_e, p_l)$ on the scalp surface, and a formula (6) is provided herein:

$$P(l|c,p) = P(l|c) \quad (6)$$

Therefore, the Markov chain frequently used by a person skilled in the art is used in the two-step stochastic process. It is assumed that points on a cortex (domain c) are a subset of points in a brain (domain b), and P(l|p) may be calculated by using P(c|p) in the formula (3) and P(l|b) in the formula (4). Specifically, if p and c are discretized, the Chapman-Kolmogorov equation is indicated as follows:

$$P(l_k|p_i) = \sum_{j=1}^{N_c} P(l_k|c_j) \times P(c_j|p_i) \quad (7)$$

where $p_i$ is a discretized location (that is, any point, similarly below) in a CPC space, where $i=1, 2, \ldots, N_p$; $c_j$ is a discretized location of C in the standard brain space, where $j=1, 2, \ldots, N_c$; and $l_k$ is an atlas label of a particular brain atlas, where $k=1, 2, \ldots, N_l$.

It should be noted that, the transcranial brain atlas constructed in the foregoing steps is a probability atlas. That is, when a probe of a transcranial device (which includes but is not limited to a transcranial brain imaging apparatus such as fMRI or fNIRS or a transcranial brain treatment apparatus such as rTMS) performs stimulation or recording at any location p having given coordinates on a scalp surface, a probability that each targeted brain region labeled by l is probed may be given by using the transcranial brain atlas. According to the transcranial brain atlas, invisible intracerebral atlas label information is projected onto a visible scalp, so that a researcher or a doctor may directly use these pieces of brain structure information and function atlas information, thereby greatly improving the function of the brain atlas in the transcranial brain mapping technology.

The transcranial brain atlas generation method constructed in the present invention is described above on the whole. During actual application, an obvious individual difference exists between cranial shapes and brain structures of persons. How to extend the foregoing transcranial brain atlas constructed by collecting an individual characteristic to a group level, so as to include common characteristics of an intracerebral structure as many as possible and screening individual differences of the intracerebral structure as few as possible becomes another technical task to be urgently resolved by researchers or doctors in the field.

For this purpose, in an embodiment of the present invention, an MRI data set of 114 participants is used, an example of constructing a transcranial brain atlas based on a conventional brain atlas is provided, the constructed transcranial brain atlas is verified, and repeatability and predictability of the transcranial brain atlas provided in the present invention are confirmed.

In the second step of the foregoing two-step stochastic process, this embodiment of the present invention is implemented by using three general brain atlases in an existing brain imaging technology. The first brain atlas is an LPBA atlas (LONI Probabilistic Brain Atlas), $P_{LPBA}(l|b)$, where a cortical structure of a brain is labeled based on macroscopic anatomical parcellation in a standard brain space (Shattuck, 2008). The second brain atlas is an AAL labeling atlas (Automated Anatomical Labeling Atlas), $P_{AAL}(l|b)$, where a macroscopic anatomical structure of a region of interest in each hemisphere is labeled in a brain of a single subject in a standard brain space (Tzourio-Mazoyer et al., 2002). The last brain atlas is a Talairach atlas, $P_{BA}(l|b)$, where 47 Brodmann areas (BA) labels are defined in a brain of a single subject by using a cell type in the Brodmann's scheme (Talairach and Tournoux, 1988; Lancaster et al., 2000).

Below, a process of generating a group-level transcranial brain atlas based on the LPBA atlas and an application result of the transcranial brain atlas based on the LPBA atlas are described first, and repeatability and predictability of the transcranial brain atlas are described.

A structural MRI (sMRI) data set of 114 youth participants (age: 18 to 24, 63 females, and 51 males) in the SLIM database (Southwest University Longitudinal Imaging Multimodal) (http://fcon_1000.projects.nitrc.org/indi/retro/southwestuni_qiu_index.html) is used. High-resolution 3D T1-weighted structural images are obtained by using a Magnetization-Prepared Rapid Acquisition Gradient Echo (MPRAGE) sequence (TR/TE=1900 ms/2.52 ms, FA=9°, FOV=256×256 mm$^2$; slices=176; thickness=1.0 mm; voxel size=1×1×1 mm$^3$).

For each participant, four cranial landmarks Nz, AL, AR, and Iz are visually identified in an individual-level 3D MRI image by using MRIcron software (a schematic diagram of identifying a cranial landmark is shown in FIG. 2), and then a scalp surface and a cortical surface are extracted. Specifically, each individual 3D MRI image is segmented into six tissue images: gray matter, white matter, cerebrospinal fluid (CSF), bone, soft tissue, and air/background by using a unified segmentation algorithm in SPM12 (Wellcome Trust Centre for Neuroimaging, London, UK. Http://www.fil.ion.ucl.ac.uk/spm). A brain image (gray matter+white matter) and a head image (gray matter+white matter+CSF+bone+soft tissue) are generated. After the brain image and the head image are smoothed by using a Gaussian kernel and FWHM [3, 3, 3] and binarized by using a threshold of 0.5, the surface extraction algorithm in SPM12 is applied to the binarized images to extract a scalp surface point cloud (in pink) and a cortical surface point cloud (in gray) of a participant (as shown in FIG. 1b).

On the basis of determining the four cranial landmarks Nz, AL, AR, and Iz, the landmark Cz is marked in the individual scalp surface point cloud by using the iterative algorithm provided by Jurcak et al. (with reference to Jurcak, V., D. Tsuzuki, and I. Dan, 10/20, 10/10, and 10/5 systems revisited: their validity as relative head-surface-based positioning systems. Neuroimage, 2007. 34(4): p. 1600-11.) Then, a group-level transcranial brain mapping model is generated by using a formula (8):

$$P(c_j|p_i) = \frac{\text{total number of individuals whose } CPC \text{ point } p_i \text{ is mapped to an } MNI \text{ location } c_j}{\#} \quad (8)$$

where $p_i$ is a grid location in CPC, where $i=1, 2, \ldots, N_p$; $c_j$ is a cortical voxel in the standard brain space obtained by using a transcranial brain mapping technology, where $j=1, 2, \ldots, N_c$; and # is a total number of individuals. For example, a transcranial brain mapping model 114 list of any point p(0.4, 0.6) on a scalp surface is given in FIG. 4, and a color block on a gray brain model in FIG. 4 indicates spatial frequency distribution P(c|p) of cortical projection points corresponding to the given cranial surface coordinate point p=(0.4, 0.6).

In consideration of a discretized form required by the formula (8), in this embodiment of the present invention, a continuous CPC space is discretized by evenly segmenting an entire range of either of $p_e$ and $p_l$ into 100 segments, to generate an even grid, named CPC$_{100}$ (as shown in FIG. 3(b)). In CPC$_{100}$, a distance between two neighboring points is approximately less than 3.5 millimeters, and a spatial resolution is compatible with those in most transcranial brain mapping technologies.

For each point p in $CPC_{100}$, for example, (0.4, 0.6) in FIG. 4(c), the corresponding scalp location s(x, y, z) (the pink point in FIG. 4) is determined by formulas (1) and (2) from the individual scalp point cloud. Then, the mature balloon inflation model is applied to the scalp location s(x, y, z) to determine a corresponding cortical location (the yellow point in FIG. 4). Then, the cortical location (the yellow point in FIG. 4) in the individual space is spatially normalized into the standard brain space to obtain c. All (s, c) pairs are aggregated to generate an individual-level transcranial brain mapping model, that is, obtain mapping from the $CPC_{100}$ grid to the standard brain space.

During actual calculation, MNI coordinates of the cortical projection point are adjusted. First, MNI coordinates of all projection points are spatially re-sampled according to the resolution of the atlas image. Second, MNI coordinates of few cortical projection points are modified. Due to a registration error, after few cortical projection points are normalized into the standard brain space, the normalized cortical projection points are beyond the range of the brain atlas. During actual calculation, these deviated points are modified, and the deviated projection points are limited, by using Nearest Neighbor Searching, to being within the spatial range of the brain atlas.

As a result, a matrix of mapping from a CPC coordinate point to a voxel of an atlas may be obtained. For example, for the LPBA atlas, 136020 gray matter voxels exist in total. Through cranio-cerebral projection and spatial normalization, cranio-cerebral mapping of each subject may be indicated as a 9801×136020 binary matrix. A frequency is calculated for a point in the binary matrix at a group level, to obtain a matrix $Matrix_{PB}$, and a row in $Matrix_{PB}$ indicates a distribution law of an estimated conditional probability. For the AAL atlas, the size of $Matrix_{PB}$ is 9801×185355. For the BA atlas, the size of $Matrix_{PB}$ is 9801×403482.

The atlas information is converted into a matrix of mapping from a voxel to a region label according to the information provided in the brain atlas image. For the AAL atlas and the BA atlas, probability distribution is explicitly given in a file of the brain atlas image. Therefore, the following is defined:

$$P\{L = l_k | B = b_j\} = \begin{cases} 1, \text{ when a landmark } l_k \text{ is endowed with an } MNI \text{ coordinate } b_j \\ 0, \text{ when a landmark } l_k \text{ is not endowed with an } MNI \text{ coordinate } b_j \end{cases} \quad (9)$$

Accordingly, a region label is converted into a probability form.

For the LPBA atlas, the information provided in the brain atlas image directly gives a probability that each label occurs at each spatial location. Therefore, brain region voxels in the brain atlas image are directly indexed one by one, and probability values of each label in the voxels are recorded.

For a location in the entire standard brain space, an event in which the location does not belong to any labeled region exists, and a complementary event of this event is that the location is at least labeled as a brain region. "None-brain" is explicitly used as a special brain region label, and a probability of none-brain is defined as:

$$P\{L = noneBrain | B = b_j\} = 1 - \sum_k P\{L = l_k\} \quad (9)$$

A conditional probability P(L|B) satisfies a probability property:

$$\sum_k P\{L = l_k\} = 1 \quad (10)$$

The foregoing obtained conditional probability distribution is marked as a matrix form $Matrix_{BL}$. For the AAL atlas, the size of $Matrix_{BL}$ is 136020×121. For the BA atlas, the size of $Matrix_{BL}$ is 185355×47. For the LPBA atlas, the size of $Matrix_{BL}$ is 1336020×57.

A matrix $Matrix_{PL}$ of probability mapping from a cranial coordinate to a brain region label is solved according to $Matrix_{PB}$ and $Matrix_{BL}$ obtained in the foregoing steps, where $$Matrix_{PL} = Matrix_{PB} \cdot Matrix_{BL}$$

For the LPBA atlas, the size of $Matrix_{PL}$ is 9801×57. For the AAL atlas, the size of $Matrix_{PL}$ is 9801×121. For the BA atlas, the size of $Matrix_{PL}$ is 9801×47. A row in $Matrix_{PL}$ indicates a mapping probability of mapping a given CPC cranial coordinate location to each region label; and a column in $Matrix_{PL}$ indicates a conditional probability $P(L=l_k|P)$ of mapping a CPC coordinates to a given brain region label $l_k$, and this probability indicates a possibility that each CPC coordinate point corresponds to $l_k$.

A first step of presenting the transcranial brain atlas is to determine positioning of two hemispheres and four main lobes in the CPC space. A main-lobe-level transcranial brain atlas is constructed and presented in FIG. 5(a) and FIG. 5(b). It can be learned from the maximum-likelihood labeling map (MLM) in FIG. 5(b) that, an original spatial topology such as a bilateral symmetry among the four lobes in the brain space is reserved in the CPC space. A maximum probability map (MPM) in FIG. 5(a) indicates a relatively high consistency of labels in the transcranial brain atlas at a population level (median=0.946). Moreover, an obvious narrow boundary in FIG. 5(a) roughly corresponds to a sulcus structure for dividing a brain lobe.

Figure 5:
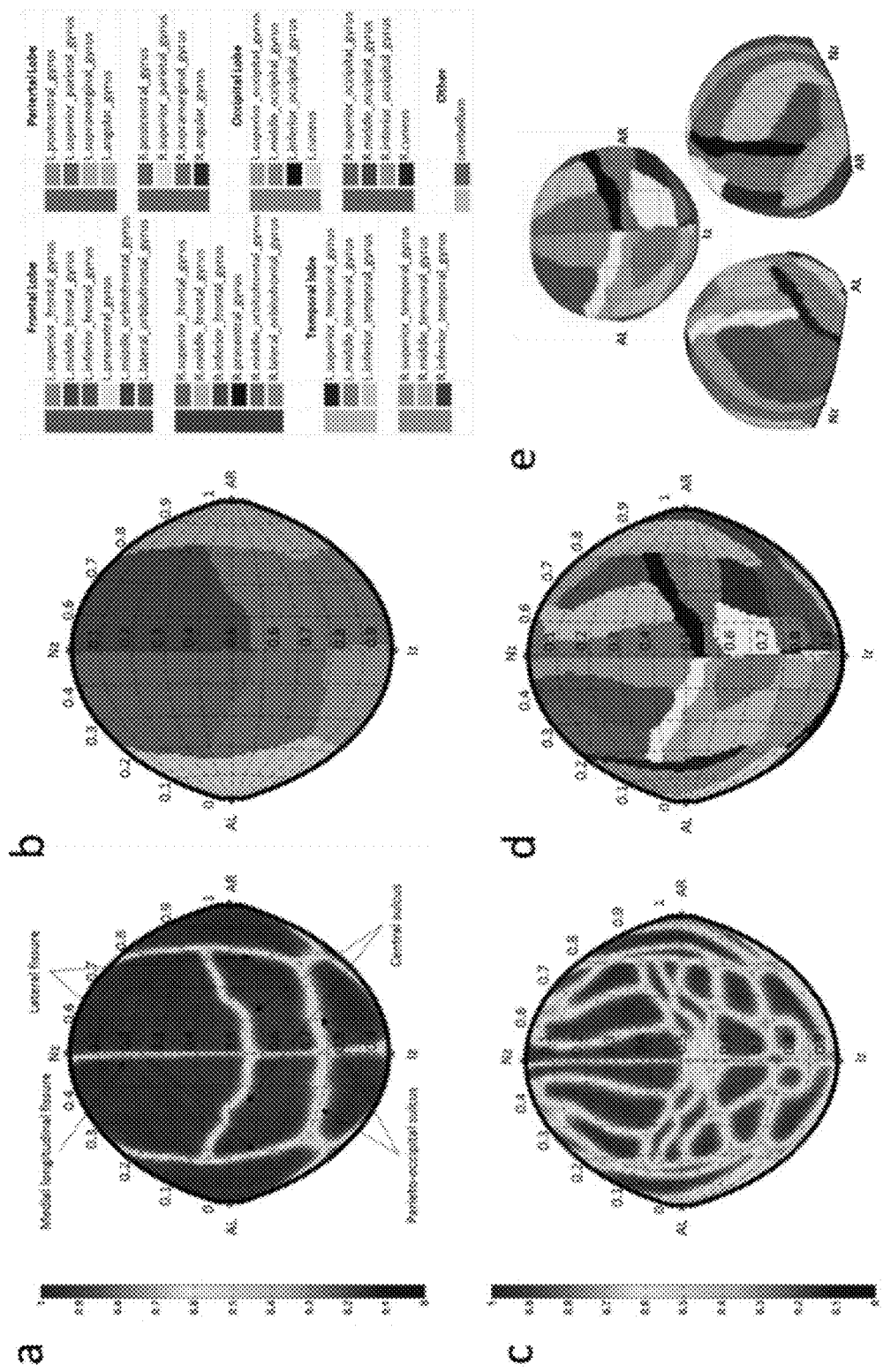
FIG. 5 is a schematic diagram of TBA_LPBA.

In this embodiment of the present invention, a transcranial brain atlas with 35 sub-regions (TBA_LPBA) is presented on the BNU map (shown in FIG. 5(d)) and a stereotaxic scalp surface in three different views (FIG. 5(e)) with a color coding scheme inherited from the LPBA atlas. There are 56 sub-regions in the original LPBA atlas, but 21 sub-regions are invisible in the transcranial brain atlas. The invisible sub-regions are mainly located in medial and ventral parts of the brain, and are inaccessible to the transcranial brain mapping technology. Moreover, visible but small sub-regions in the transcranial brain atlas may correspond to large structures in the original brain atlas. For example, the pre-cuneus is such a sub-region, most parts of which are located within the medial longitudinal fissure, and therefore the sizes of the same labeled regions between the transcranial brain atlas and the corresponding brain atlas are not necessarily comparable. The MPM of TBA_LPBA in FIG. 5(c) shows high consistencies (up to 98%) in each sub-region while low consistencies only occur near boundaries.

To sum up, in the present invention, a probabilistic framework based on the two-step Markov chain model is first provided as theoretical foundation of the transcranial brain atlas. The first step is the cranio-cortical mapping from the scalp locations in the CPC space to the underlying cortical locations in the MNI space. The second step is to construct the transcranial brain atlas by using the conventional brain atlas, which is actually mapping from the cortical location in the MNI space to the label space of the atlas. It should be noted that, in the present invention, an extensible transcranial brain atlas model is provided by using the probability framework, and the brain atlas used in the foregoing second step may be replaced with any other brain atlas. In the present invention, only three brain atlases (the BA atlas, the AAL atlas, and the LPBA atlas) based on the macroscopic anatomy are provided to construct the transcranial brain atlas, but similar functional atlases, connection atlases, and other atlases may be used to provide a functional transcranial brain atlas for a particular application.

The effectiveness of the transcranial brain atlas is mainly embodied in two main aspects. First, construction of the transcranial brain atlas is to estimate population-level anatomical information by sampling some individuals of a population. Therefore, results of construction of the transcranial brain atlas on different sampling of the population should be consistent. Secondly, the transcranial brain atlas finally needs to use group-level anatomical knowledge, to implement positioning and navigation for individual transcranial data. Therefore, group-individual predictability implemented based on the transcranial brain atlas is also another important index for evaluating the effectiveness of the transcranial brain atlas.

To verify the constructed transcranial brain atlas, the performance of the transcranial brain atlas is quantized in two manners in this embodiment of the present invention. First, repeatability of the transcranial brain atlas is measured. For the transcranial brain atlas, high repeatability means that group-level transcranial brain atlases constructed from different samples of a same group are similar. The second effectiveness index is predictability. High predictability means that an individual-level transcranial brain atlas may be replaced with a group-level transcranial brain atlas at a relatively high confidence level. If there is a lack of an individual structure image, this means that an experimenter may predict probe placement on the head of an individual subject or patient by using the group-level transcranial brain atlas.

In order to evaluate the repeatability of the group-level transcranial brain atlas, in this embodiment of the present invention, a structural sMRI data set of 114 participants is randomly divided into two groups (GA and GB), and each group has 57 participants. GA and GB are respectively used to construct a transcranial brain atlas 57A and a transcranial brain atlas 57B. The repeatability of the group-level transcranial brain atlas is evaluated by estimating the consistency between the transcranial brain atlas 57A and the transcranial brain atlas 57B. A DICE index is used to evaluate the labeling consistency for each labeled region l. The DICE index is calculated by using maximum likelihood landmarks ($l^*_{57A}(P)$ and $l^*_{57B}(p)$) of the transcranial brain atlas 57A and the transcranial brain atlas 57B:

$$DICE(l) = \frac{2|X_{lA} \cap X_{lB}|}{|X_{lA}| + |X_{lB}|} \quad (12)$$

where ∥ gives the area within a labeled region, and $X_{lA}$ and $X_{lB}$ are respectively regions having a label l in $l^*_{57A}(p)$ and $l^*_{57B}(p)$. DICE indexes range from 0 to 1, and a larger value indicates higher consistency.

For calculated DICE values (Median=0.95), refer to Table 1.

TABLE 1

Region DICE value of TBA_LPBA

| brain region label (l) | DICE |
|---|---|
| R.inferior_temporal_gyrus | 0.98 |
| R.middle_frontal_gyrus | 0.98 |
| R.angular_gyrus | 0.98 |
| R.inferior_frontal_gyrus | 0.97 |
| R.superior_frontal_gyrus | 0.97 |
| L.superior_parietal_gyrus | 0.97 |
| R.middle_temporal_gyrus | 0.97 |
| R.superior_parietal_gyrus | 0.97 |
| L.middle_occipital_gyrus | 0.97 |
| R.supramarginal_gyrus | 0.96 |
| L.middle_frontal_gyrus | 0.96 |
| L.superior_frontal_gyrus | 0.96 |
| R.lateral_orbitofrontal_gyrus | 0.96 |
| L.lateral_orbitofrontal_gyrus | 0.96 |
| L.inferior_frontal_gyrus | 0.96 |
| R.precentral_gyrus | 0.95 |
| R.middle_occipital_gyrus | 0.95 |
| L.angular_gyrus | 0.95 |
| L.supramarginal_gyrus | 0.95 |
| L.middle_temporal_gyrus | 0.95 |
| L.inferior_temporal_gyrus | 0.94 |
| R.postcentral_gyrus | 0.94 |
| L.superior_occipital_gyrus | 0.94 |
| L.postcentral_gyrus | 0.92 |
| R.superior_occipital_gyrus | 0.92 |
| L.precentral_gyrus | 0.92 |
| R.superior_temporal_gyrus | 0.91 |
| R.middle_orbitofrontal_gyrus | 0.91 |
| R.inferior_occipital_gyrus | 0.89 |
| cerebellum | 0.86 |
| L.superior_temporal_gyrus | 0.83 |
| L.middle_orbitofrontal_gyrus | 0.79 |
| L.inferior_occipital_gyrus | 0.70 |
| L.cuneus | 0.67 |
| R.cuneus | 0.20 |

In order to quantitatively investigate prediction accuracy, the sMRI data from the 114 participants is randomly divided into a construction group (GC, 92 participants) and a testing group (GT, 22 participants). A transcranial brain atlas constructed based on the construction group is used to predict an individual-level transcranial brain atlas of each participant in the testing group. That is, a maximum likelihood label from the group-level transcranial brain atlas is compared with a corresponding label from the individual-level transcranial brain atlas. For each CPC point p, a correct rate of a prediction accuracy is calculated, to obtain a prediction accuracy map.

Figure 6:
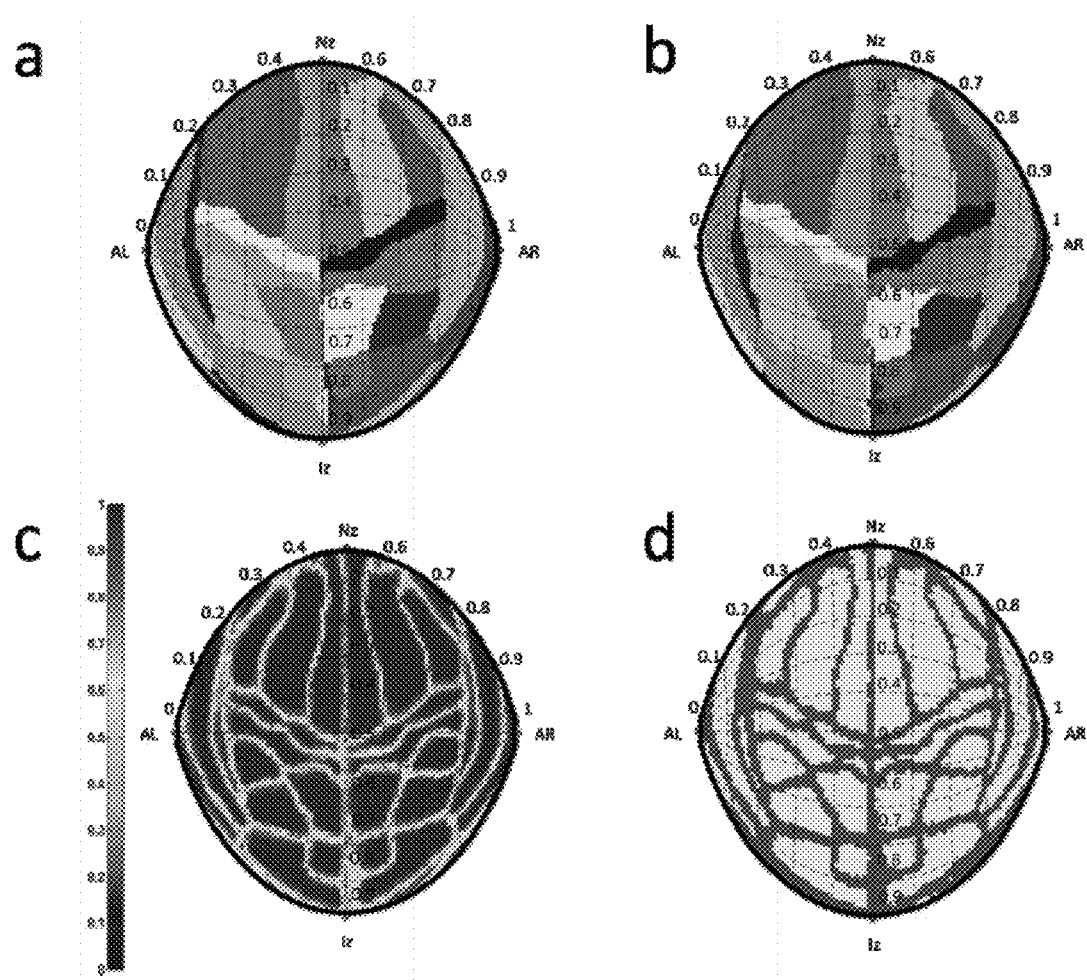
FIG. 6 is a schematic diagram of a predictive result of group-level TBA_LPBA for an individual.

An individual-level transcranial brain atlas of any participant in the testing group shown in FIG. 6(a) is quite similar to a predicted transcranial brain atlas (that is, a transcranial brain atlas 92) shown in FIG. 6(b). The group-level prediction accuracy map (FIG. 6(c)), summarizing all the 22 individual prediction performances, demonstrates an overall high prediction accuracy (Median=0.96). In FIG. 6(d), a region coded with yellow has an accuracy higher than 90%, while a region coded with red has a prediction accuracy lower than 90%. It may be learned from FIG. 6(d) that, a region having a slightly low accuracy is located near a boundary. In order to evaluate the predictability of the constructed group-level transcranial brain atlas for other race of participants, a group formed of 24 Caucasian participants (age: 23.43±4.6; 17 males and 7 females) is used as another testing group, to obtain a slightly lower prediction accuracy (Median=0.92).

The prediction results of transcranial brain atlas_AAL and transcranial brain atlas_BA continue to be simply described below.

76 sub-regions exist in transcranial brain atlas_AAL, where 44 sub-regions of 120 sub-regions (60 sub-regions exist on each hemisphere) in the original AAL atlas are invisible. The MPM demonstrates an overall high labeling consistency (Median=0.86) and low consistencies occurring only in smaller sub-regions and near boundaries, especially in the occipital lobe and near the lateral sulcus. The regional DICE values are quite high (Median=0.86). The median of the group-level prediction accuracy is up to 0.91, indicating an overall high prediction accuracy. In order to evaluate the predictability of the constructed transcranial brain atlas for other participants, a group of 24 Caucasian participants (age: 23.43±4.6; 17 males and 7 females) is used as another testing group, resulting in a slightly lower prediction accuracy (Median=0.88).

27 sub-regions exist in transcranial brain atlas_BA, where 23 sub-regions of 50 sub-regions in the original Talairach atlas are invisible. The MPM also demonstrates an overall high labeling consistency (median=0.87) but low consistencies occurring in long and narrow sub-regions near the central sulcus and the lateral sulcus. The regional DICE values are quite high (Median=0.92). The median of the group-level prediction accuracy is up to 0.91, indicating an overall high prediction accuracy. In order to evaluate the predictability of the constructed transcranial brain atlas 114 for other participants, a group of 24 Caucasian participants (age: 23.43±4.6; 17 males and 7 females) is used as another testing group, resulting in a slightly lower prediction accuracy (Median=0.88).

An important conclusion may be drawn from the foregoing research: Although a difference exists between individuals, cortical projection points corresponding to same cranial landmark points of different subjects have a correspondence at a brain gyrus level or a brain atlas region level. On one hand, this correspondence ensures placement of a transcranial imaging apparatus based on a cranial location, and can ensure a consistency between different persons at the gyrus level. On the other hand, corresponding cortical locations of 10 to 20 verified landmark points may be used to predict, independent of individual anatomical or brain imaging information, a cortical location that may be probed by the transcranial imaging apparatus.

It should be noted that, for some transcranial mapping technologies such as fNIRS, additional sMRI scanning is seldom conducted. Fortunately, the group-level transcranial brain atlas can be used herein as existing knowledge, to show a most probable placement location for a particular target, and a most probable anatomical label for each scalp location. As described above, the predictability of the group-level transcranial brain atlas is verified. The experiment proves that, on our data, median prediction accuracy is higher than 0.9, and errors occur mostly near boundaries of label regions. For other transcranial mapping technologies (for example, TMS) in which more emphasis is placed on accuracy, sMRI scanning is more common. When sMRI data is available, an individual-level transcranial brain atlas can be further constructed based on the individual transcranial model, thereby providing more assured labeling accuracy.

On the basis of the foregoing group application oriented transcranial brain atlas generation method and prediction method, the present invention further provides a transcranial brain atlas prediction apparatus that may be applied to clinic treatment. In an embodiment of the present invention, the transcranial brain atlas prediction apparatus may be made into a shape of a helmet or a head cap, so as to cover a relatively complete scalp surface. A group-level transcranial brain atlas image obtained by using the present invention may cover an upper surface of the transcranial brain atlas prediction apparatus in a printing or spray painting manner, and a lower surface of the transcranial brain atlas prediction apparatus is tightly attached to a scalp surface of a user during actual use.

Figure 7:
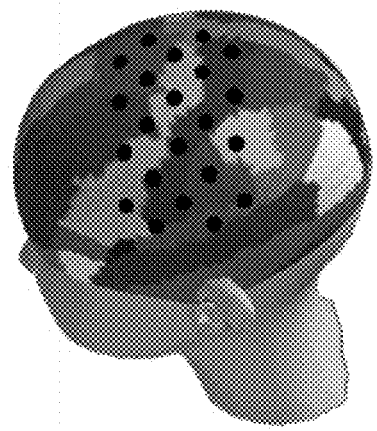
FIG. 7 is a schematic diagram of an embodiment of a transcranial brain atlas prediction apparatus according to the present invention.

Referring to FIG. 7, in a variant example of the foregoing embodiment, the transcranial brain atlas prediction apparatus may be simplified as a head cap that is similar to a swimming cap and on which a group-level transcranial brain atlas image is printed. The head cap is made of a cotton cloth or chemical fiber material with low costs, and it is convenient to perform large-scale promotion and use. In practice, when an individual-level transcranial brain atlas image of a user is obtained by using the foregoing transcranial brain atlas generation method, the image may be directly spray-painted or printed on a blank head cap, thereby presenting, on the head cap, the transcranial brain atlas image reflecting an individual characteristic of the user. When being under corresponding brain clinic treatment, the user may carry the head cap to help a doctor perform accurate positioning.

A plurality of small holes is distributed on a surface of the transcranial brain atlas prediction apparatus, so as to enable a probe of a transcranial imaging apparatus or a transcranial treatment apparatus to be in contact with the scalp surface of the user through the foregoing small holes, thereby implementing a corresponding intracranial brain observation or treatment operation. The foregoing small holes for the probe to pass through are preferably arranged into a dot matrix shape according to different sub-regions in the group-level transcranial brain atlas image, where for a sub-region whose area is relatively small, the arrangement density of small holes may be larger (that is, the small holes are arranged more densely); and for a sub-region whose area is relatively large, the arrangement density of small holes may be smaller (that is, the small holes are arranged relatively sparsely). In this way, it may be ensured that when the probe is operated in different sub-regions, the probe can find a sufficient operation location regardless of the area of a region.

Compared with the conventional brain atlas, the transcranial brain atlas provided in the present invention can effectively resolve the positioning problem in the transcranial brain imaging research. First, through establishment of a cranial coordinate system, an entire cranial surface space, that is, a placement space of the transcranial imaging apparatus can be precisely described, to ensure repeatability of the placement location between different individuals. Second, a correspondence between a standard cranial space and a standard brain space enables a researcher or a doctor to directly obtain corresponding MNI space coordinates from the placement location of the transcranial imaging apparatus on a cranial bone, so as to resolve the problem of positioning transcranial data without an MRI structure image. Third, information about a brain label on a cranial surface of a subject is reversely displayed, so as to visually guide accurate placement of the transcranial imaging apparatus.

According to the transcranial brain atlas provided in the present invention, invisible intracerebral atlas label information is projected onto a visible scalp, so that a researcher or a doctor may "directly" use these pieces of brain structure information and function atlas information, thereby greatly improving the function of the brain atlas during use of the transcranial brain mapping technology.

The group application oriented transcranial brain atlas generation method, prediction method, and prediction apparatus provided in the present invention are described in detail above. Any obvious change made to the present invention by a person of ordinary skill in the art without departing from the essential spirit of the present invention will constitute a violation of the patent right of the present invention and will bear a corresponding legal liability.

What is claimed is:

1. A transcranial brain atlas generation method, comprising the following steps:
    (1) creating a cranial surface coordinate system at an individual level, the step (1) comprises the following substeps:
        (11) identifying five cranial landmarks Nz, Iz, AL, AR, and Cz on a scalp surface;
        (12) defining an intersection curve between the scalp surface and a plane passing through Nz, Cz, and Iz as a cranial equator;
        (13) giving a point p on the scalp surface, wherein a longitude curve can be uniquely determined as an intersection curve between the scalp surface and a plane passing through AL, AR, and p, and p' is an intersection point between the cranial equator and the longitude curve; and
        (14) uniquely determining any point p on an upper scalp by using a pair of non-negative real numbers $(p_e, p_l)$:

$$p_e = L_{Nz-p'}/L_e, p_e \in [01]$$

$$p_l = L_{AL-p}/L_{AL-p-AR}, p_l \in [01]$$

wherein $L_{Nz-p'}$ is a curve length from Nz to p' along the cranial equator, and $L_e$ is a full length of the cranial equator; and $L_{AL-p}$ is a curve length from AL to p along the longitude curve whose full length is $L_{AL-p-AR}$;
    (2) establishing a transcranial mapping system used to connect a cranial location and a brain location; and
    (3) constructing a transcranial brain atlas by using a two-step stochastic process in a Markov chain.

2. The transcranial brain atlas generation method according to claim 1, wherein step (1) further comprises step (15): establishing a CPC space on a standard hemisphere;
    and planarizing a hemisphere having CPC coordinates by using a Hammer-Aitoff projection, to generate a map having a CPC coordinate system presented on a flat ellipse.

3. The transcranial brain atlas generation method according to claim 1, wherein step (2) comprises the following substeps:
    determining an underlying cortical location c corresponding to the given any point p on the scalp surface in an individual space by using a balloon inflation model; and
    after all cortical locations are spatially normalized into an MNI space, aggregating all (p, c) pairs, to generate a deterministic individual transcranial brain mapping model.

4. The transcranial brain atlas generation method according to claim 3, wherein step (2) further comprises the following step:
    integrating all individual models to generate a group-level probabilistic transcranial brain mapping model: P(c|p), wherein $p(p_e, p_l) \in CPC$, $c(x, y, z) \in C$, and C is a subset of the MNI space.

5. The transcranial brain atlas generation method according to claim 4, wherein in the step (2), the probabilistic transcranial brain mapping model is generated according to the following formula:

$$P(c_j|p_i) = \frac{\text{total number of individuals whose } CPC \text{ point } p_i \text{ is mapped to an } MNI \text{ location } c_j}{\#}$$

wherein $p_i$ is a $CPC_{100}$ grid location, wherein i=1, 2, ..., $N_p$; $c_j$ is a cortical voxel in the MNI space obtained by using a transcranial brain mapping technology, wherein j=1, 2, ..., $N_c$; and # is a total number of individuals.

6. The transcranial brain atlas generation method according to claim 4, wherein step (3) further comprises the following steps:
    (31) mapping a given point p ($p_e$, $p_l$) to a cortical location c (x, y, z) in the MNI space through probabilistic transcranial mapping P(c|p); and
    (32) mapping the cortical location c (x, y, z) to a label l in a label space L.

7. The transcranial brain atlas generation method according to claim 6, wherein in the step (3), assuming that points on a cortical domain c are a subset of points on a cerebral domain b, if p and c are discretized, P(l|p) is indicated by using a Chapman-Kolmogorov equation:

$$P(l_k|p_i) = \sum_{j=1}^{N_C} P(l_k|c_j) \times P(c_j|p_i)$$

wherein $p_i$ is a discretized location in a CPC space, wherein i=1, 2, ..., $N_p$; $c_j$ is a discretized location of C in the MNI space, wherein j=1, 2, ..., Nc; and $l_k$ is a label of a particular brain atlas, wherein k=1, 2, ..., $N_l$.

8. The transcranial brain atlas generation method according to claim 6, wherein in the step (32), any one of an LPBA40 brain atlas, an AAL labeling atlas or a Talairach atlas is used.

9. The transcranial brain atlas generation method according to claim 1, further comprising step (4):
    generating a maximum likelihood labeling map and/or a maximum probability map.

10. A group application oriented transcranial brain atlas prediction method, comprising the following step:
    for an independent individual in a group, when a probe of a transcranial device performs stimulation or recording at any location on a scalp surface having given coordinates, giving, by using the transcranial brain atlas according to claim 1, a probability that each targeted brain region is probed.

11. The transcranial brain atlas prediction method according to claim 10, wherein
    the transcranial device is any one of a transcranial brain imaging apparatus or a transcranial brain treatment apparatus.

12. A group application oriented transcranial brain atlas prediction apparatus, wherein
    the transcranial brain atlas prediction apparatus is in a shape of a helmet or a head cap, and has an upper surface covered with the transcranial brain atlas according to claim 1 and a lower surface tightly attached to a scalp surface of a user during use.

13. The transcranial brain atlas prediction apparatus according to claim 12, wherein
    a plurality of small holes is distributed on a surface of the transcranial brain atlas prediction apparatus, so as to enable a probe of a transcranial device to be contact with the scalp surface of the user through the small holes.

14. The transcranial brain atlas prediction apparatus according to claim 12, wherein
the small holes are arranged into a dot matrix shape according to different sub-regions in a transcranial brain atlas image, and have an arrangement density reversely changed according to the area of the sub-regions.

* * * * *